(12) United States Patent
McEwen et al.

(10) Patent No.: US 8,568,441 B2
(45) Date of Patent: Oct. 29, 2013

(54) MANUFACTURE AND USE OF TOURNIQUET CUFF WITH IMPROVED PNEUMATIC PASSAGEWAY

(75) Inventors: James A. McEwen, Vancouver (CA); Kenneth Glinz, Richmond (CA); Kevin B. Inkpen, Vancouver (CA); Michael Jameson, North Vancouver (CA)

(73) Assignee: Western Clinical Engineering Ltd., Vancouver (CA)

( * ) Notice: Subject to any disclaimer, the term of this patent is extended or adjusted under 35 U.S.C. 154(b) by 0 days.

(21) Appl. No.: 13/080,265

(22) Filed: Apr. 5, 2011

(65) Prior Publication Data
US 2011/0184457 A1 Jul. 28, 2011

Related U.S. Application Data

(63) Continuation of application No. 11/153,667, filed on Jun. 15, 2005, now abandoned.

(51) Int. Cl.
*A61B 17/00* (2006.01)
(52) U.S. Cl.
USPC .................................................. 606/202
(58) Field of Classification Search
USPC .................. 606/202, 203, 201; 600/490, 499; 602/13; 128/118.1
See application file for complete search history.

(56) References Cited

FOREIGN PATENT DOCUMENTS

| GB | 436730 | 4/1934 |
|---|---|---|
| JP | H9-117419 | 5/1997 |
| JP | H11-512630 | 11/1999 |
| JP | 2004-73402 | 3/2004 |
| WO | 9712556 | 4/1997 |

OTHER PUBLICATIONS

English translation of JPO Office action in corresponding Patent App JP2011-233525, Mar. 19, 2013; 7 pages.

*Primary Examiner* — Thomas McEvoy
(74) *Attorney, Agent, or Firm* — Hancock Hughey LLP

(57) ABSTRACT

Disclosed are methods of manufacturing and inflating an elongated bladder of a tourniquet cuff that may be secured around the limb of a patient. The method includes sealing together side edges of layers of material to form the bladder, and stiffening the cuff with a stiffener for compressing the portion of the bladder underlying the stiffener inwardly toward the limb while preventing two layers of the cuff from contacting each other at a location adjacent to an edge of the cuff to thus provide a continuous pneumatic passageway in the bladder between the overlying stiffener and the sealed edge for distributing inflating gas through the passageway along the length of the bladder. The method also includes separating the layers that form the bladder with a flange member that together with the bottom layer of the bladder defines a channeled passageway extending away from a port opening in the bladder for delivering gas through the channeled passageway, beyond the flange member and into the inflatable bladder, such that pressurized gas received in the port opening is directed through the channeled passageway and toward the continuous pneumatic passageway that is adjacent to the sealed edge.

22 Claims, 5 Drawing Sheets

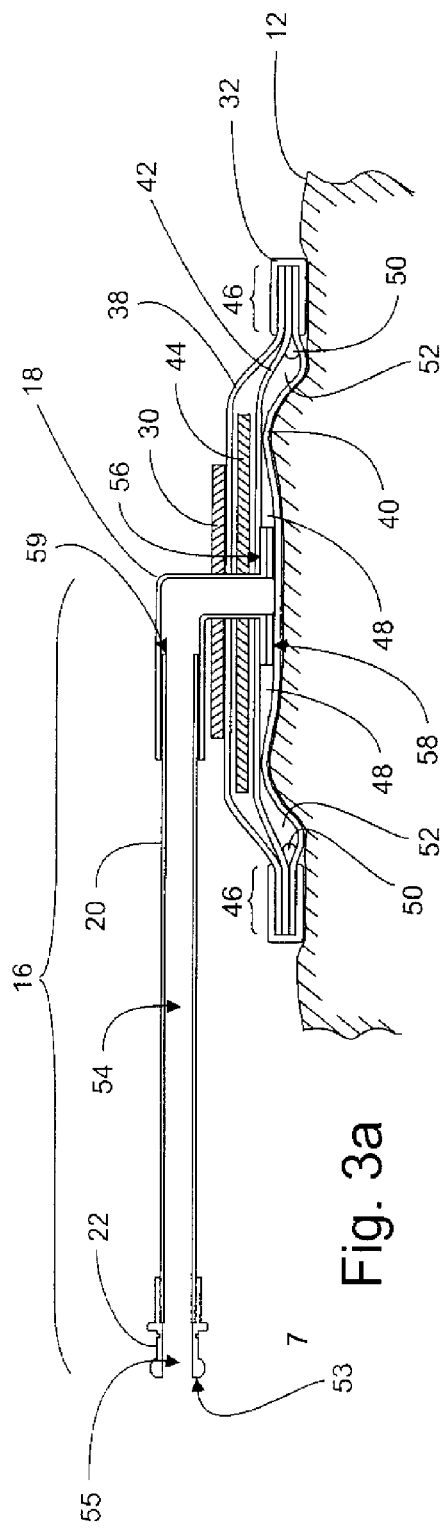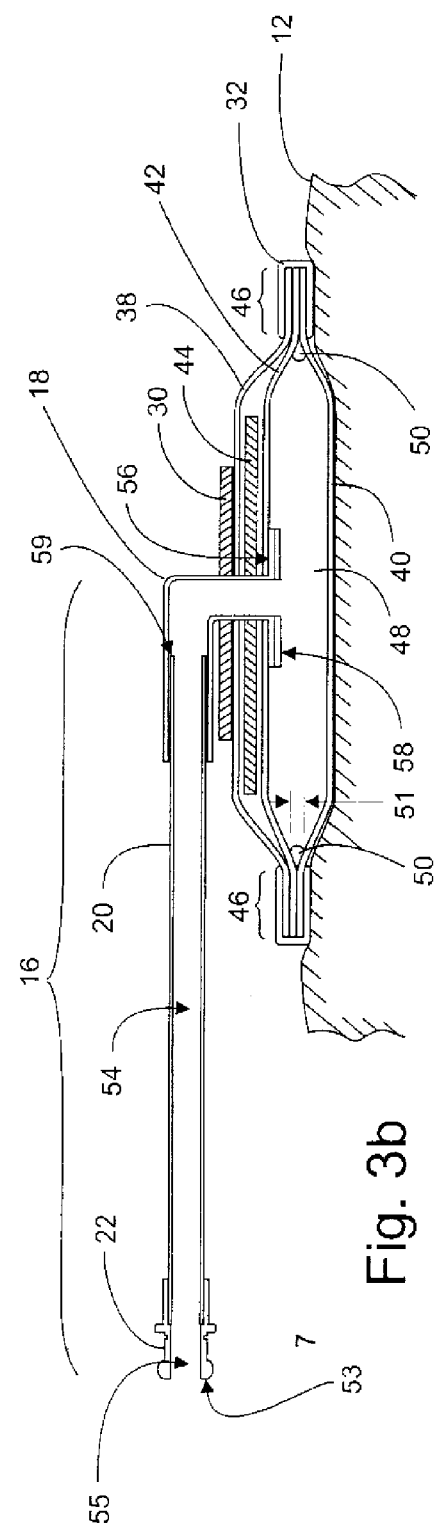

MANUFACTURE AND USE OF TOURNIQUET CUFF WITH IMPROVED PNEUMATIC PASSAGEWAY

FIELD OF THE INVENTION

This invention pertains to pneumatic tourniquet cuffs commonly used for stopping arterial blood flow into a portion of a surgical patient's limb to facilitate the performance of a surgical procedure, and for facilitating intravenous regional anesthesia.

BACKGROUND OF THE INVENTION

A typical surgical tourniquet system of the prior art includes a tourniquet cuff for encircling a patient's limb at a desired location and a tourniquet instrument that includes flexible instrument tubing for connecting to the tourniquet cuff. The tourniquet cuff typically includes an inflatable portion, and the inflatable portion of the cuff is typically connected through a cuff port having a port connector to the flexible instrument tubing of the tourniquet instrument, thereby establishing a pneumatic passageway from the tourniquet instrument through the instrument tubing and the cuff port into the inflatable portion of the cuff. In some prior-art systems, the tourniquet instrument includes a pressure transducer to sense the pressure of gas at the instrument end of the pneumatic passageway and to enable the sensed pressure to be displayed for surgical staff. Some prior-art tourniquet instruments include a pressure regulator to increase and decrease the pressure of gas in the pneumatic passageway, and to maintain the pressure in the inflatable portion of the cuff at a pressure above a minimum pressure required to stop arterial blood flow past the cuff during a time period suitably long for the performance of a surgical procedure. Many types of pneumatic surgical tourniquet systems, including tourniquet cuffs and tourniquet instruments, have been described in the prior art, such as those described by McEwen in U.S. Pat. Nos. 4,469,099, 4,479,494, 5,439,477 and by McEwen and Jameson in U.S. Pat. Nos. 5,556,415 and 5,855,589.

Some tourniquet cuffs of the prior art have only a single port for connection to the tourniquet instrument and thus establish only a single pneumatic passageway between a tourniquet instrument and the inflatable portion of such cuffs. The pressure in the inflatable portion of such single-port tourniquet cuffs must be sensed indirectly from the tourniquet instrument, through the same pneumatic passageway that is used by the tourniquet instrument to increase, decrease and regulate cuff pressure during surgery. The flow resistance of the pneumatic passageway affects the accuracy and speed of regulation of pressure within the inflatable portion of such single-port tourniquet cuffs as well as the accuracy of the indirectly sensed tourniquet cuff pressure.

Other tourniquet cuffs of the prior art have dual ports to establish two separate pneumatic passageways between the tourniquet instrument and the inflatable portion of the cuff, to achieve increased safety and performance by enabling the tourniquet instrument to provide surgical staff with a more accurate indication of cuff pressure and by enabling the tourniquet instrument to increase the speed and accuracy of cuff pressure regulation. Representative dual-port tourniquet cuffs of the prior are described in U.S. Pat. Nos. 4,635,635, 5,454,831, 5,439,477, 5,741,295 and 5,649,954. In one dual-port tourniquet system of the prior art, described in U.S. Pat. No. 4,469,099, the pneumatic pressure regulation elements within the tourniquet instrument communicate with the inflatable portion of the tourniquet cuff through one pneumatic passageway of the tourniquet cuff, and a pressure sensor within the tourniquet instrument communicates pneumatically with the inflatable portion of the cuff through a separate pneumatic passageway of the cuff.

With both single and dual-port tourniquet systems, the speed and accuracy of pressure regulation and indication are improved if flow restrictions in the pneumatic passageway are minimized. Typical port connectors of the prior art have a male barbed connection portion which fits inside the pneumatic passageway of the port, creating a region of reduced pneumatic flow area and increasing flow resistance between the cuff and the tourniquet instrument.

One hazard associated with all pneumatic tourniquet cuffs of the prior art is the obstruction of the pneumatic passageway within the cuff. For example, in a single-port tourniquet cuff, a complete obstruction within the pneumatic passageway may allow the actual pressure in the inflatable portion of the cuff to decrease substantially below the desired tourniquet pressure to a level where the cuff may be completely depressurized, or to increase substantially above the desired tourniquet pressure, without any indication to the surgical staff. In effect, the monitoring and regulation of cuff pressure by a prior-art tourniquet instrument stops at the location of the obstruction. As another example, a complete obstruction within a region of the inflatable portion of the cuff may isolate all or part of the inflatable portion and thus may prevent the pressure throughout the entire inflatable portion of the cuff from being sensed and regulated near the desired pressure by the tourniquet instrument. Any isolated region may be hazardous, either by permitting arterial blood to flow into the limb past a region of lower cuff pressure or by requiring surgical staff to set the tourniquet instrument to an unnecessarily high pressure to stop blood flow past the cuff. Also, any complete obstruction of the pneumatic passageway within a tourniquet cuff of the prior art may render ineffective any audio-visual safety alarms of a connected prior-art tourniquet instrument intended to warn of hazardous over-pressurization or under-pressurization of the cuff, such as the safety alarms described by McEwen in U.S. Pat. No. 4,469,099.

Another hazard associated with tourniquet cuffs of the prior art is partial obstruction of the pneumatic passageway. A partial obstruction of the pneumatic passageway at the port connector, or elsewhere within the port or inflatable portion of a prior-art cuff may increase the pneumatic flow resistance at the partial obstruction, and thus may affect the ability of a connected tourniquet instrument to rapidly and accurately regulate pressure past the partial obstruction and throughout the inflatable portion of the tourniquet cuff. Increased flow resistance from a partial obstruction may also reduce the ability of a connected tourniquet instrument to accurately and rapidly indicate changes of the pressure in the tourniquet cuff to surgical staff. Further, a partial obstruction of the pneumatic passageway within a region of the inflatable portion of the cuff may affect the ability of the tourniquet instrument to uniformly regulate pressure throughout the entire inflatable portion of the cuff.

In addition to the hazards of complete and partial obstructions that may affect the integrity of the pneumatic passageway, another hazard associated with prior-art cuffs is the interruption of the passageway due to unanticipated detachment of the port connector from the tourniquet instrument, or detachment of the port connector from the port, thus separating the inflatable portion of the tourniquet cuff from the tourniquet instrument. A related hazard is a leak at the port connector that is sufficiently large to prevent a connected tourniquet instrument from maintaining cuff pressure near the desired pressure. Such a large leak may result, for example, from deterioration or deformation of the connector of a single-use disposable tourniquet cuff as a result of reprocessing and reuse of the disposable tourniquet cuff in multiple surgical procedures in a manner neither intended nor anticipated by the manufacturer.

Many disposable tourniquet cuffs of the prior art are designed to be used in only one single surgical procedure and then discarded. Many such disposable tourniquet cuffs are sterilized at time of manufacture and supplied to users as sterile products, because such cuffs are typically intended to be suitable for use within sterile surgical fields. As a result, the design characteristics of such prior-art cuffs are intended to allow them to be applied and used safely and reliably within a sterile surgical field during one surgical procedure, and to be discarded cost-effectively after that procedure. For example, some disposable tourniquet cuffs of the prior art have a port that includes a very flexible thermoplastic tubing portion having a length sufficient to allow a user to easily bend the port away from the surgical site and position the port connector beyond the sterile surgical field. Although such long and flexible port tubing facilitates connection of the port to non-sterile instrument tubing away from the sterile surgical field, it may also increase the possibility of partial or complete obstruction of the pneumatic passageway within the port, for example by accidental kinking, bending, or pinching of the tubing. The various materials and components from which such prior-art disposable tourniquet cuffs are assembled are chosen to be sufficiently inexpensive to allow the cuff to be economically discarded after a single use, and also to be capable of sterilization by exposure to a specific sterilizing agent within a specific sterilizing process determined by the manufacturer, with no significant deterioration or change of properties that would impair the safety or performance of the cuffs after such sterilization.

Efforts have been made to reprocess and reuse tourniquet cuffs of the prior art that were originally supplied by their manufacturers as sterile, single-use products. Reprocessing efforts typically involve saving rather than discarding a disposable tourniquet cuff after surgery, visually examining the cuff to identify any obvious deterioration that might suggest reprocessing is not appropriate, attempting to remove any blood and other surgical debris by washing the cuffs with water combined with any of a variety of detergents or other cleaning liquids, in some cases conducting some functional tests of the cuff, re-packaging the cuff and then sterilizing the re-packaged cuff by exposing it to a sterilization agent within a sterilization process that may be different from that determined by the original manufacturer to be safe and effective. Reprocessing of disposable tourniquet cuffs may be carried out within hospitals or surgery centers or by third-party reprocessors, and the quality and methods of reprocessing are highly variable.

Reprocessing, cleaning and re-sterilizing of disposable tourniquet cuffs may result in hazards for the surgical patients on whom such cuffs are subsequently used. The hazard arises from the use of any of a variety of chemical or physical agents that are attendant with the reprocessing, cleaning or re-sterilizing processes. For example, exposure of a cuff to liquids during cleaning may allow the liquids to enter the pneumatic passageway of the cuff, where they may remain to partially or complete obstruct the pneumatic passageway of the cuff within the port or inflatable portion. Water remaining within the pneumatic passageway after cleaning may subsequently react chemically with ethylene oxide, a sterilizing agent commonly used in reprocessing, to form ethylene glycol, a sticky substance that may completely or partially block the pneumatic passageway. Exposure of prior-art cuffs to sterilizing agents different than the sterilizing agent employed at the time of manufacture may produce a change and deterioration in the properties of some cuff materials and components, for example due to a chemical reaction or exposure to radiation. Exposure of a prior-art cuff containing flexible thermoplastic materials to an elevated temperature during cleaning or sterilization by known prior-art processes may soften thermoplastic materials and components, increasing the likelihood of hazardous deformation of some components. For example, an elevated temperature during reprocessing may result in substantial deformation of the thermoplastic stiffener included in some prior-art cuffs, thus impairing the application of pressure by such a cuff to an underlying limb upon subsequent use in surgery. Also, an elevated temperature during reprocessing may deform the thermoplastic connectors of some prior-art cuffs, or may weaken the retention force of typical thermoplastic barb-type port connectors, so that such connectors cannot establish or reliably maintain a gas-tight passageway between the tourniquet cuff and tourniquet instrument upon reuse. An elevated temperature associated with cleaning or re-sterilization increases the likelihood that the pneumatic passageway within the cuff may become partially or completely obstructed, as described above, as a result of such reprocessing. Repeated cleaning, re-sterilization and reuse of a disposable tourniquet cuff in multiple surgical procedures may progressively increase the hazard for the surgical patients on whom the cuff is used.

There is a need for a tourniquet cuff that has minimal flow restrictions within its pneumatic passageway under normal operating conditions, that has a substantially reduced likelihood of partial or complete obstructions or interruptions of the pneumatic passageway under foreseeable operating conditions, that can indicate exposure of the cuff to one or more external agents that are capable of affecting the integrity of the pneumatic passageway before use, and that can be manufactured economically. The present invention addresses this need.

BRIEF DESCRIPTION OF THE DRAWINGS

FIG. 3a is a section taken from FIG. 2, with the uninflated cuff applied to the patient's limb as shown in FIG. 1.

FIG. 3b is a section taken from FIG. 2, with the cuff applied to the patient's limb and inflated.

DETAILED DESCRIPTION OF THE PREFERRED EMBODIMENT

Figure 1:
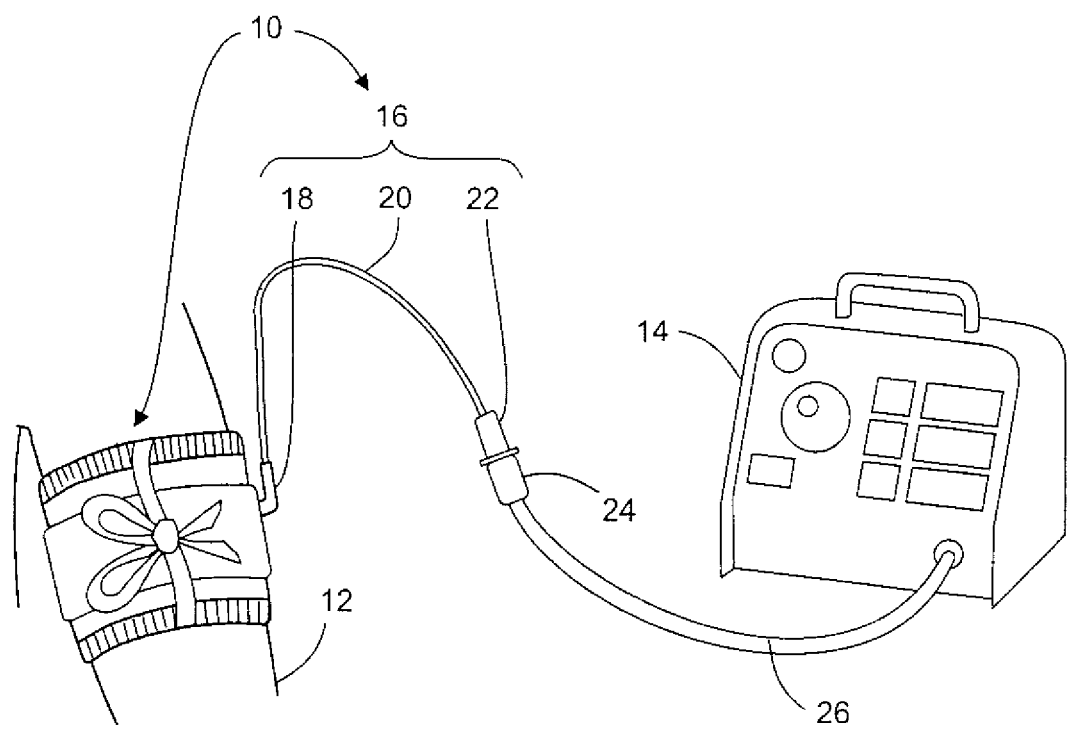
FIG. 1 is a pictorial representation of the preferred embodiment in a surgical application.

FIG. 1 is a pictorial representation of the preferred embodiment in a surgical application, showing the tourniquet cuff 10 applied to patient limb 12 and pneumatically connectable to tourniquet instrument 14. Cuff 10 includes cuff port 16, which comprises bladder sealing flange 18, port tubing 20, and port connector 22. In the preferred embodiment shown, cuff 10 is a single port cuff, where cuff port 16 provides a single pneumatic passageway to the inflatable portion of cuff 10. Those skilled in the art will appreciate that the features described in the preferred embodiment may also be applied to tourniquet cuffs having more than one port, such as those described by U.S. Pat. Nos. 4,469,099, 4,479,494, and 5,254,087. Cuff port 16 is pneumatically connected to tourniquet instrument 14 via instrument connector 24 and instrument tubing 26. In the preferred embodiment cuff port 16 is of sufficient length to allow pneumatic connection between cuff 10 and instrument 14 to be made outside a sterile surgical field. Port connector 22 is a locking connector (based on the connector of the tourniquet cuff described by McEwen in U.S. Pat. No. 5,649,954 and similar in some design aspects to connector DSM2202, Colder Products Company, St. Paul, Minn.) which allows cuff port 16 to form a releasable pneumatic connection with instrument connector 24.

As described below, cuff 10 is constructed of materials that are appropriate for a single-use sterile disposable tourniquet cuff. To permit cuff 10 to be used in a sterile surgical field, cuff 10 is sterilized at time of manufacture by exposure to a sterilizing agent within a sterilizing process determined to be safe and effective. To prevent deterioration of the cuff, and to maintain the integrity of the pneumatic passageways within cuff 10, a sterilization agent and process that will not harm the materials or components of cuff 10 is selected by the manufacturer. In the preferred embodiment cuff 10 is sterilized by exposure to gamma radiation or electron beam radiation.

The cost of materials is an important consideration in the manufacture of tourniquet cuffs intended for a single use and then disposal. To minimize the cost of materials and assembly of cuff 10, materials are selected which are not intended to withstand exposure to subsequent sterilization and cleaning processes. The subsequent sterilization or cleaning of cuff 10 by agents and processes commonly used in health care facilities, such as ethylene oxide gas sterilization, hydrogen peroxide gas sterilization, high temperature and pressure steam sterilization, sterilization by other chemical agents, and pasteurization, are all capable of adversely affecting the integrity of the pneumatic passageways of cuff 10. As described further below, cuff 10 includes one or more components that act as visual indicators to warn a user that cuff 10 has been subjected to a subsequent sterilization or cleaning process capable of adversely affecting cuff 10 and that cuff 10 may no longer be safe to use.

Figure 2:
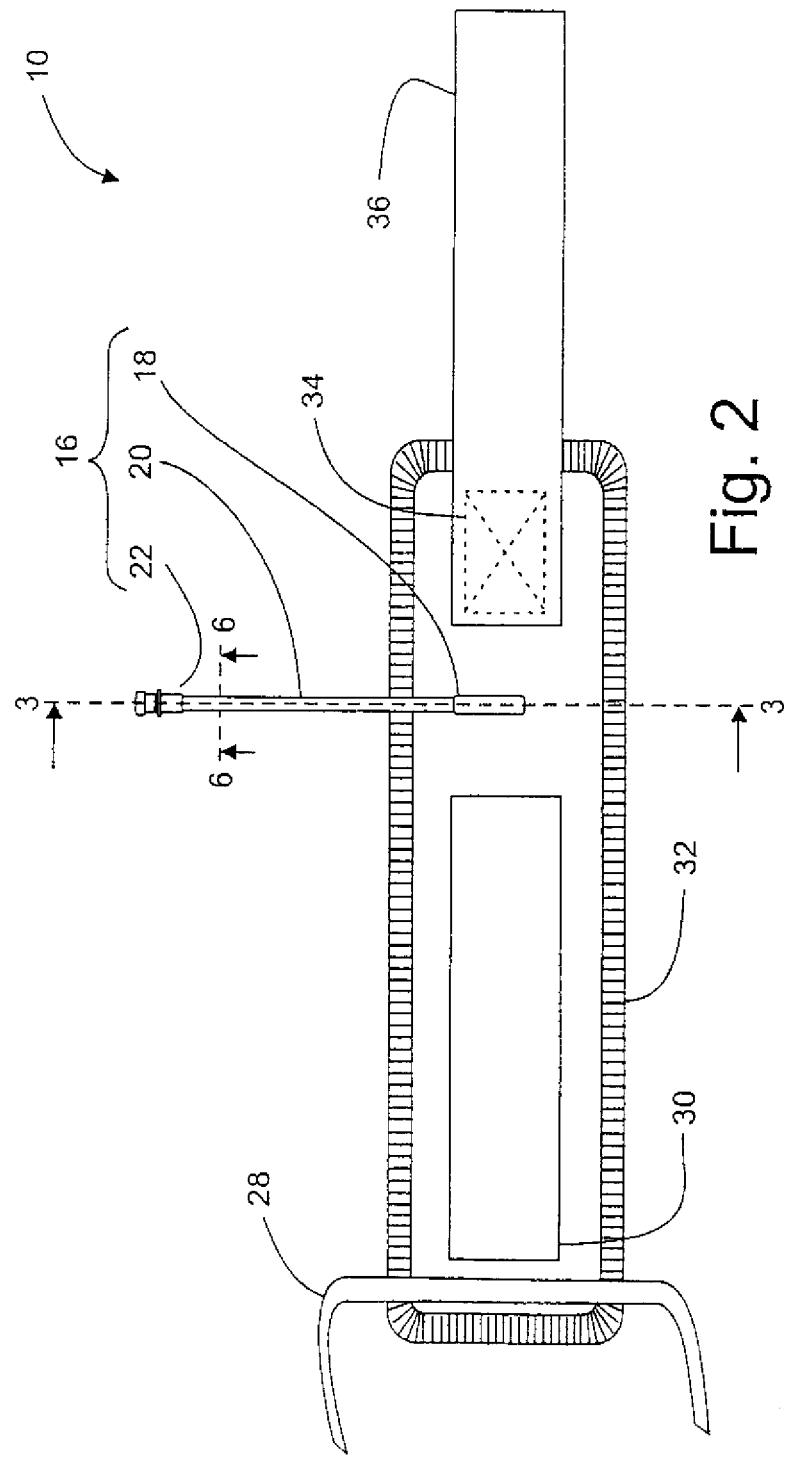
FIG. 2 shows the cuff portion of the preferred embodiment.

FIG. 2 shows the cuff 10 of the preferred embodiment, which is similar in design and construction to the cuffs described by McEwen in U.S. Pat. Nos. 5,741,295, 5,649,954, 5,484,831 and by Robinette-Lehman in U.S. Pat. No. 4,635,635. In the preferred embodiment shown, cuff 10 is rectangular with a length sufficient to encircle an adult arm as shown in FIG. 1. Those skilled in the art will appreciate that the features described in the preferred embodiment may also be incorporated in cuffs of various sizes and shapes, such as those described by McEwen in U.S. Pat. No. 5,649,954. In addition to cuff port 16, cuff 10 comprises tie ribbon 28, loop material 30, edge trim 32, sewn joint 34, and hook material 36. In use, cuff 10 is wrapped snugly around the limb 12 (see FIG. 1) and secured circumferentially around the limb when the user engages hook material 36 to loop material 30. Tie ribbon 28 is a soft fabric ribbon material (Grosgrain ⅝" wide, Dynatex Textiles Inc., Toronto, Ontario, Canada) and allows the user to pull cuff 10 snug around the limb. When cuff 10 is in position and secured circumferentially around the limb, the user ties tie ribbon 28 as shown in FIG. 1 to help prevent the cuff from sliding proximally or distally on the limb when inflated. Edge trim 32 is made of similar material to tie ribbon 28 and helps prevent chafing of the patient's limb by the edges of cuff 10.

FIG. 3a is a section taken from FIG. 2, however with cuff 10 applied to the limb 12 (as shown in FIG. 1) and cuff 10 uninflated. Top layer 38 and bottom layer 40 are made of woven nylon cloth coated with thermoplastic material (for example, 200 Denier nylon cloth coated in thermoplastic polyurethane 0.006" thick) on the surfaces that face middle layer 42. Middle layer 42 is made of thermoplastic sheet material (for example, 0.020" thick polyurethane). Stiffener 44 is made of plastic sheet cut to a rectangular shape fitting within the perimeter of cuff 10. The stiffener 44 has greater stiffness than layers 38, 40, and 42 but is flexible enough to be wrapped around the limb (for example 0.020" thick polyethylene sheet). Top layer 38, middle layer 42, and bottom layer 40 are joined around a continuous perimeter within the perimeter of cuff 10 at bladder seal 46, thereby forming inflatable bladder 48 between middle layer 42 and bottom layer 40 and enclosing thermoplastic stiffener 44 between top layer 38 and middle layer 42. Bladder 48 therefore has a width at the port location as shown in FIG. 3a, a typical value being 3.5 inches, and a length extending along the length of the cuff (see FIG. 2) and sufficient to encircle the limb. When secured circumferentially around the limb as shown in FIG. 1, stiffener 44 helps direct the expansion of inflatable bladder 48 radially inwards towards the limb upon inflation of the cuff. The stiffener thus provides uniformly distributed pressure onto limb 12.

Bladder seal 46 is formed by a heat and pressure joining process, typically radio-frequency welding using a selected sealing die. The heat of the joining process is selected to temporarily melt a portion of the thermoplastic materials in layers 38, 40, and 42, causing them to fuse together in the area of bladder seal 46. The pressure of the joining process in combination with the shape of the sealing die is selected to squeeze a predetermined portion of the melted thermoplastic materials in layers 38, 40, and 42 out of the area of bladder seal 46, forming a continuous bead 50 along the perimeter of inflatable bladder 48. When the joining process is complete, bead 50 solidifies back to the original rigidity of the thermoplastic materials in layers 38, 40, and 42 and has thickness 51 (shown in FIG. 3b only for clarity). Thickness 51 is proportional to the selected amount of thermoplastic material squeezed out during the formation of bladder seal 46, and is selected to be large enough to form and maintain bladder pneumatic passageway 52 when bottom layer 40 is compressed against middle layer 42 during certain conditions of use, which are described in more detail below.

Cuff port 16 of cuff 10 comprises port connector 22, port tubing 20, and bladder sealing flange 18, which are permanently joined together with pneumatically sealed joints to form port tubing pneumatic passageway 54 and port connector pneumatic passageway 55 (see FIG. 7a) which form a continuous pneumatic passageway extending from distal port end 53 to inflatable bladder 48. Bladder sealing flange 18 has flange top surface 56 which is permanently joined to middle layer 42 by a heat sealing process similar to that used to form bladder seal 46 (as described above). Bladder sealing flange 18 also has bottom surface 58. Port tubing 20 has a length between bladder end 59 and port connector 22, which is at minimum greater than the bladder width at the port location, and preferably 30 inches, which is sufficient to extend outside the sterile surgical field. Bladder sealing flange 18 forms a portion of pneumatic passageway 54 extending from port tubing bladder end 59 and formed to enter inflatable bladder 48 in a direction normal to top surface 56 and bottom surface 58 of bladder sealing flange 18, and thereby normal to the area of middle layer 42 around bladder sealing flange 18.

FIG. 3b is a section taken from FIG. 2, however with cuff 10 applied to the limb 12 (as shown in FIG. 1) and cuff 10 inflated. Inflatable bladder 48 is shown expanded radially inwards towards the limb.

Figure 4:
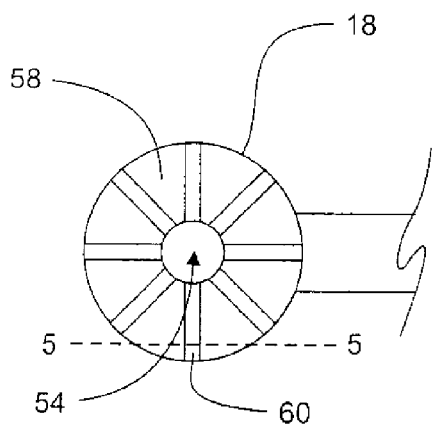
FIG. 4 is a view looking on the bottom surface of the bladder sealing flange.

FIG. 4 is a view looking on bottom surface 58 of bladder sealing flange 18. Bladder sealing flange 18 is made of thermoplastic polyurethane by injection molding (in a similar manner to existing sealing flanges such as 167ACU-BK, Halkey Roberts Corp., St. Petersburg, Fla. which are currently used in tourniquet cuffs). A plurality of channels 60 are formed in surface 58 extending from the outer perimeter of flange 18 to port pneumatic passageway 54.

Figure 5:
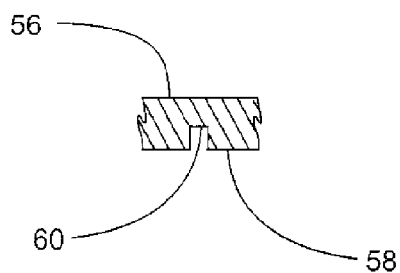
FIG. 5 is a section taken from FIG. 4.

FIG. 5 is a section taken from FIG. 4, showing a typical channel 60 formed in the area between flange bottom surface 58 and flange top surface 56. Because bladder sealing flange 18 must be heat sealed to middle layer 42, channels 60 may be formed in to surface 58 by correspondingly shaped ridges on the sealing die and therefore are formed during the heat sealing process of bladder sealing flange 18 to middle layer 42 with no additional per item cost compared to the typical prior-art cuffs.

Referring to FIGS. 1, 3a, 4, and 5, when port connector 22 is connected to instrument 14, a pneumatic passageway is established from instrument 14 through port pneumatic passageway 54 (formed by the openings in port connector 22, port tubing 20, and bladder sealing flange 18), channels 60 in bladder sealing flange bottom surface 58 into inflatable bladder 48. Bead 50 acts to hold open the bladder 48 near the bladder seal 46 thereby establishing a bladder pneumatic passageway 52 around the perimeter of inflatable bladder 48, allowing pneumatic communication throughout the bladder.

If bladder sealing flange 18 is compressed against limb 12 (for example if the flange area of the cuff is lying between the limb and the operating room table or bolster on which the limb is resting, or cuff 10 is applied to limb 12 too tightly), bottom layer 40 may be pressed against flange bottom surface 58 as shown in FIG. 3a. On bladder sealing flanges typically used in tourniquet cuffs of the prior art (for example see 167ACU-BK, Halkey Roberts Corp., St. Petersburg, Fla.), surface 58 is flat and smooth. Using prior-art flanges in the condition shown in FIG. 3a, pneumatic communication between inflatable bladder 48 and port pneumatic passageway 54 is closed off or restricted. In the current invention, however, channels 60 form a plurality of pneumatic passageways between inflatable bladder 48 and port pneumatic passageway 54 in the area between flange bottom surface 58 and flange top surface 56, which remain open when bottom layer 40 is compressed against flange bottom surface 58.

Furthermore, if any area of the cuff containing inflatable bladder 48 is compressed against the limb, bottom layer 40 may be pressed against middle layer 42 in some areas (as shown in FIG. 3a) which may restrict or close pneumatic communication between different regions of inflatable bladder 48. Bead 50 separates middle layer 42 and bottom layer 40, thereby establishing bladder pneumatic passageway 52 extending around the entire perimeter of inflatable bladder 48 as noted above. The size of bead 50 is selected such that bladder pneumatic passageway 52 is maintained under the compression forces between bottom layer 40 and middle layer 42 expected in surgical use, thereby maintaining pneumatic communication among all regions of bladder 48.

In addition to the conditions described above which may occur during the normal use of cuff 10, exposure of cuff 10 to an elevated temperature or pressure, or exposure of cuff 10 to certain chemicals, or a combination of these conditions may occur during storage, shipping, or subsequent cleaning and sterilization processes and may cause bottom layer 40 to adhere to flange bottom surface 58 or areas of middle layer 42 by softening the thermoplastic materials. If the materials adhere, pneumatic passageways will nonetheless be maintained by bead 50 and channels 60.

Figure 6A:
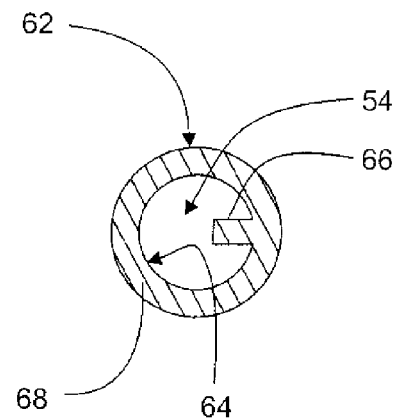
FIG. 6a is a section taken from FIG. 2, showing the preferred embodiment.
Figure 7A:
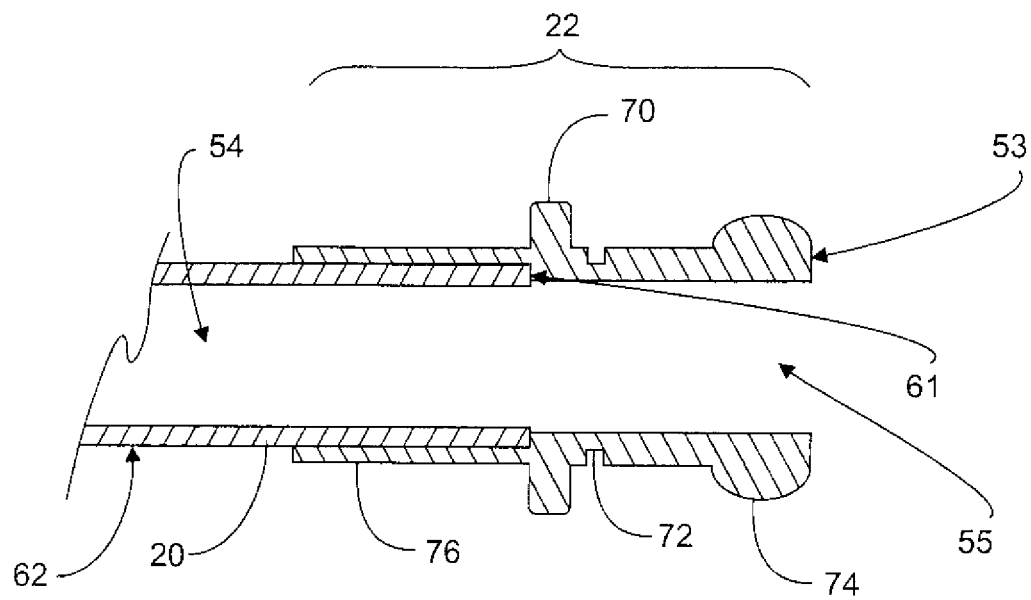
FIG. 7a is a detail view of the areas indicated in FIG. 3a and FIG. 3b, showing the preferred embodiment.

FIG. 6a is a section taken from FIG. 2, showing the cross-sectional profile of port tubing 20 of cuff port 16, extending from bladder end 59 (see FIGS. 3a and 3b) to port tubing end 61 (see FIG. 7a). Port tubing 20 is formed by an extrusion process and is made of a blend of thermoplastic polyurethane and sterilization indicator formulated to change color when exposed to certain agents that, as noted above, may have a deleterious effect on the integrity of the pneumatic passageway. In this embodiment, the sterilization indicator does not react to change color during the initial sterilization of cuff 10 by gamma or electron beam radiation at time of manufacture. In the preferred embodiment, the thermoplastic material is formulated to undergo a distinct and permanent color change upon exposure to predetermined minimum levels of one or more selected sterilizing agents different than the agent employed at time of manufacture and typical of those commonly used within health care facilities and by reprocessors. Ethylene oxide gas is one such secondary sterilizing agent that may be used in a reprocessing sterilization process. Other agents are hydrogen peroxide gas, high temperature steam, and other chemical sterilizing agents. This color change occurs over the length of port tubing 20 and is visually perceptible by the user to indicate that cuff 10 has undergone a subsequent sterilization capable of affecting the pneumatic communication described above and shown in FIG. 3a. To enhance the appearance of the color change that takes place within port tubing 20 upon exposure to a subsequent sterilizing process, a portion of port tubing 20 may be marked with a substance that does not change color upon exposure to the sterilization process. For example, port tubing 20 may be formed from a thermoplastic material that normally has a clear color and changes to a brown color upon exposure to the ethylene oxide sterilization process. Port tubing 20 may also be marked with a white stripe which runs the length of port tubing 20. When port tubing 20 is exposed to the sterilization process the printed white stripe provides visual contrast to the underlying, brown colored tubing.

In the preferred embodiment the secondary sterilization indicator described above is formulated from a color-forming compound pre-selected to react with a predetermined minimum level of ethylene oxide in a secondary sterilization process. Color-forming compounds such as 4-(hydrazinocarbonyl) pyridine, 4-nitrobenzylpyridine, or other pyridines that react with ethylene oxide may be used alone or in combination to produce a non-reversible color change reaction upon exposure to ethylene oxide gas. The color-forming compound may also include catalysts that further promote the color change reaction. To increase utility, the secondary sterilization indicator of the preferred embodiment may be mixed with additional color-forming compounds known in the art that react to change color in the presence of hydrogen peroxide gas or high temperature steam. The sterilization indicator may also include other non-reactive pigments pre-selected to enhance the visibility of the color-forming compound in its reacted state, thereby making a color change more visually perceptible by a user.

To further indicate to a user that cuff 10 has been exposed to a second sterilization agent within a sterilization process different than that used at time of manufacture, the secondary sterilization indicator may be carried on another component of cuff 10, such as a label attached to cuff 10, or the surface of port tubing 20 or the surface of tie ribbon 28. For example, tie ribbon 28 may be selected to be initially white in color and upon the subsequent sterilization of cuff 10 by ethylene oxide sterilization change color to brown.

To indicate exposure of cuff 10 to a physical agent such as heat at a temperature that is capable of deforming, obstructing or otherwise adversely affecting the integrity of pneumatic passageways 54 or 55 or portions of inflatable bladder 48, an irreversible thermochromic indicator compound is carried on a selected surface of cuff 10, for example a surface of port tubing 20. Thermochromic indicators are known in the art and may be formulated to react by irreversibly changing color at a predetermined temperature to indicate that exposure to the predetermined temperature has taken place. The preferred thermochromic indicator is unaffected by the initial sterilization of cuff 10 at time of manufacture. By carrying the preferred thermochromic indicator on a selected surface of cuff 10, an indication perceptible by a user of cuff 10 is produced when cuff 10 has been exposed to a potentially damaging and hazardous temperature. Alternately, exposure of cuff 10 to an elevated temperature that is potentially damaging and hazardous may be indicated by a temperature-indicating compound that liquefies at the predetermined temperature. For example, a temperature-indicating compound (Tempilaq G TL0175, Tempil Inc., South Plainfield, N.J., which is applied like paint, re-liquifies upon reaching the predetermined temperature, then re-solidifies upon cooling below the predetermined temperature) may be carried on port tubing 20. Port tubing 20 of the preferred embodiment is made of a transparent thermoplastic polyurethane having a clear color and thus a distinct pattern of temperature-indicating compound having a different color may be applied or printed in a particular pattern along inner surface 64 so that, if inner surface 64 reaches or exceeds the predetermined temperature, the compound reacts by liquefying and, causing the pattern to spread out and change to a colored smear. This distinct change of the printed pattern carried on inner surface 64 provides a visual indication perceptible by a user cuff 10 has been exposed to an elevated temperature at least equal to the predetermined temperature and that cuff 10 thus may be unsafe to use.

A water-indicating compound (such as a water-soluble ink) may be formed into a printed pattern carried on a selected surface of cuff 10, as described in the preceding paragraph for an elevated temperature-indicating compound. Introduction of water or other liquid agents into pneumatic passageway 54 during any reprocessing could partially or completely obstruct pneumatic passageway 54. Moreover, the water could indirectly obstruct the passageway by reacting chemically with secondary sterilizing agents such as ethylene oxide. A water-soluble pattern of colored ink carried on inner surface 64 of port tubing 20 would react to and indicate the introduction of water into pneumatic passageway 54 by changing the pattern, and the change would be readily perceptible by a user.

It will be appreciated that the indicating compounds described above for water, temperature and secondary sterilizing agents may be used alone or in combination, and carried on selected surfaces of cuff 10 or combined when forming components of cuff 10, to indicate to a user that cuff 10 has been subjected to a subsequent sterilization or cleaning process capable of adversely affecting cuff 10 and that cuff 10 may no longer be safe to use.

Referring again to the cross-sectional profile of port tubing 20 shown in FIG. 6a, port tubing 20 has outer surface 62 having a circular cross-sectional shape, inner surface 64, and ridge 66. Outer surface 62, inner surface 64, and ridge 66 together form wall 68 having a non-uniform thickness, and pneumatic passageway 54 which has a non-circular cross-sectional shape. Ridge 66 protrudes into pneumatic passageway 54 and thereby prevents complete occlusion of pneumatic passageway 54 if port tubing 20 is kinked or flattened. In contrast, existing flexible tubing typically used in tourniquet cuffs has inner and outer surfaces of a circular cross-sectional shape, and do not have ridge 66. Due to the stiffening properties of the cross-sectional shape shown in FIG. 6a the cross-sectional area of wall 68 is selected to be similar or less than that of existing flexible tubing currently used in disposable tourniquet cuffs, resulting in an equivalent volume of material per unit length, and the constant cross-sectional shape of port tubing 20 allows manufacture by well proven and cost-effective extrusion methods as used for prior-art tubing, resulting in a cost of manufacture of port tubing 20 that is similar to that of the prior-art tubing.

Figure 6B:
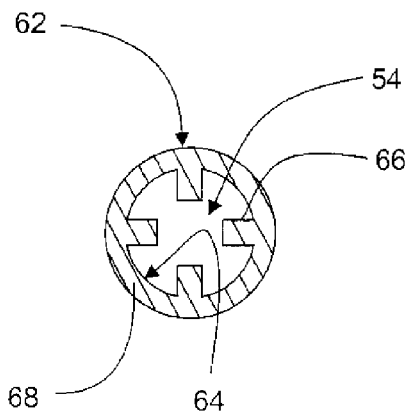
FIG. 6b is a sectional view like FIG. 6a, but showing an alternative embodiment.

FIG. 6b is a section taken from FIG. 2, showing an alternate cross-sectional profile of port tubing 20 of cuff port 16, having a plurality of ridges 66 providing increased resistance to occlusion compared to the cross section shown in FIG. 6a. Those skilled in the art will recognize that the size, shape, and number of ridges 66 may be selected to provide an anti-occlusive effect for a particular overall size and stiffness of port tubing 20, and selected to minimize the required cross-sectional area of wall 68 and thereby minimize the cost of port tubing 20.

FIG. 7a is a detail view taken from FIGS. 3a and 3b, showing the preferred embodiment. Port connector 22 is formed by an injection molding process, like the process used to form connectors of type DSM2202 (Colder Products Company, St. Paul, Minn.) that are used in commercial tourniquet cuffs derived from the cuff described by McEwen in U.S. Pat. No. 5,649,954. However, unlike these prior-art connectors, port connector 22 is made of a blend of thermoplastic polyethylene and sterilization indicator formulated to change color when exposed to the predetermined conditions described above for port tubing 20. The polyethylene component of the material used to make port connector 22 is selected to have similar stiffness, strength, sliding, and sealing properties to the polyethylene material of the connectors in the McEwen '954 cuff and of the DSM2202 connectors in related commercial cuffs of the prior art, thereby ensuring compatibility with female connectors intended for use with the DSM2202 connector. The secondary sterilization indicator of unauthorized reprocessing is as described above for port tubing 20. Alternatively or in addition, port connector 22 may carry a temperature indicating compound on one or more selected surfaces as described above for port tubing 20. Port connector 22 may also carry a water-indicating compound on one or more selected surfaces, as described above for port tubing 20.

A change in the color of port connector 22 from a first predetermined color to a second predetermined color as described above provides an indication that is visually perceptible by a user of cuff 10. Further, the above-described change of color of port connector 22 can be remotely and automatically detected by connected tourniquet instrument 14, for example by incorporating the apparatus described by McEwen in U.S. Pat. No. 6,682,547 and U.S. Patent Application No. 20030167070, both of which documents are hereby incorporated by reference. In this regard, the instrument is provided with a light emitter and light detector (such as a photodiode) arranged so that changes in the color of the port connector (or the color change of other part of the cuff that is in the optic path between the emitter and detector) will correspondingly alter the light intensity reaching the detector so that the output signal associated with the detector is indicative of the color change, hence automatically indicating the exposure to the agent that caused the color change.

Port connector 22 includes actuating flange 70, annular groove 72, and deformable ring 74 as described by McEwen in U.S. Pat. No. 5,649,954 and similar in design to the existing DSM2202 connector, thereby making port connector 22 compatible with female connectors intended for use with the DSM2202 connector. However while the prior-art connectors typically have a male barbed portion that fits inside flexible plastic tubing having a circular inner cross section, port connector 22 is adapted for easy assembly to port tubing 20 that has inner surface 64 of a non-circular cross section (see FIGS. 6a and 6b). Port connector 22 is joined to port tubing 20 by sliding female cylindrical flange 76 over outer surface 62 and bonding at the mating surface. This arrangement forms port connector pneumatic passageway 55 extending from port tubing end 61 to distal port end 53 and provides greater pneumatic flow area compared to the existing DSM2202 connector by eliminating the male barbed portion of the connector inside pneumatic passageway 54 and allowing the cross-sectional area of the port connector pneumatic passageway 55 to be equal to or greater than that port tubing pneumatic passageway 54 of port tubing 20. This greater flow area improves the speed of inflation and deflation of cuff 10 and makes pneumatic passageways 54 and 55 less likely to become occluded by kinking, compression, or debris. Furthermore bonding port connector 22 to port tubing 20 on outer surface 62 increases bond area compared to the typical arrangement seen in the prior art (inserting a male connection portion of the port connector into the inner surface of the flexible plastic tubing), which improves the strength and pneumatic sealing properties of the bond. The volume of material in female cylindrical flange 76 is similar to that of the male barbed portion of the existing DSM2202 connector, and the mold required to form female cylindrical flange 76 is simpler, so the cost of manufacture of port connector 22 is similar to or less than that of the prior-art connector.

Figure 7B:
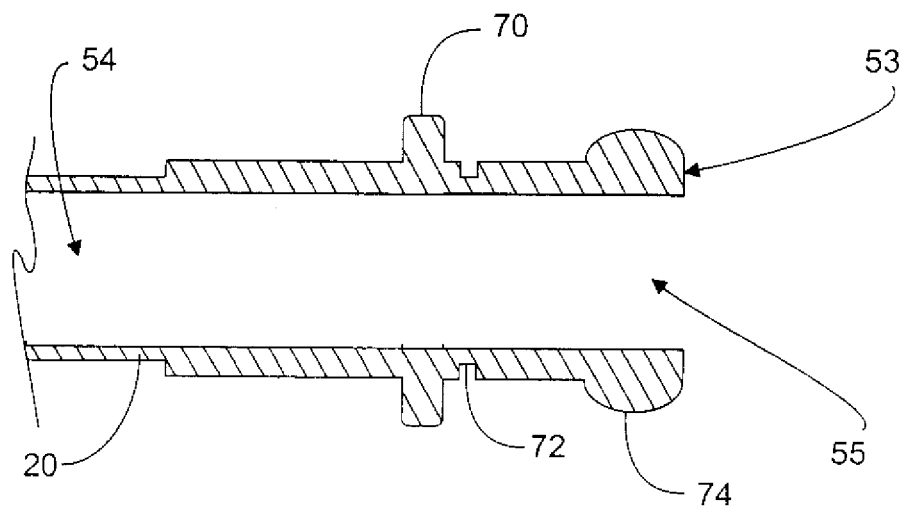
FIG. 7b is a detail view of the areas indicated in FIG. 3a and FIG. 3b, showing an alternate embodiment.

FIG. 7b is a detail view taken from FIGS. 3a and 3b, showing an alternate embodiment in which port connector 22 (see FIG. 7a) is integrated with port tubing 20 to reduce manufacturing cost. In this embodiment, the end of port tubing 20 is formed to create actuating flange 70, annular groove 72, and deformable ring 74. The thermoplastic material is as described above for port connector 22 and undergoes a distinct color change upon exposure to predetermined conditions. This alternate embodiment eliminates the assembly and bonding of port connector 22 to port tubing 20 as described in the preferred embodiment.

The invention claimed is:

1. A method of inflating with gas an elongated, inflatable, two-layer bladder of a tourniquet cuff, wherein the cuff is secured around the limb of a patient with the layers thereof pressed together, comprising the steps of:
sealing together side edges of top, middle, and bottom layers of material to form a gas-inflatable bladder between the bottom and middle layers;
stiffening the cuff with an elongated stiffener member that is enclosed within an enclosure formed between the middle and top layers, the stiffener being movable within the enclosure and arranged to compress the portion of the bladder underlying the stiffener inwardly toward the limb;
preventing the middle and bottom layers of the bladder from contacting each other at a location adjacent to a sealed edge of the bladder, thereby to provide a continuous pneumatic passageway adjacent to the sealed edge for distributing inflating gas along the length of the bladder;
limiting the width of the stiffener member to be less than the distance between the sealed side edges of the cuff thereby to prevent the stiffener from overlying and thereby compressing the continuous pneumatic passageway;
providing a port opening into the sealed bladder;
separating the middle and bottom layers that form the bladder adjacent the port opening with a flange member that together with the bottom layer defines a channeled passageway extending away from the port opening for delivering gas through the channeled passageway, beyond the flange member and into the inflatable bladder; and
receiving pressurized gas from the port opening and directing the pressurized gas through the channeled passageway and toward the continuous pneumatic passageway thereby to separate the pressed-together layers of the bladder by an amount sufficient to pneumatically connect the channeled passageway and the continuous pneumatic passageway and thereby distribute inflating gas along the length of the bladder for inflating the entire bladder to the pressure of the pressurized gas.

2. The method of claim 1 further comprising the step of providing the pressurized gas to the port opening through a tube having one end connected to the port opening and another end connectable to a tourniquet instrument that produces the pressurized gas up to a pressure level that stops blood flow in the limb past the cuff.

3. The method of claim 2 including the step of configuring the flange member for establishing adjacent to the flange a volume between the separated middle and bottom layers that is sufficiently large so that when pressurized to a level less than the pressure level that stops blood flow in the limb past the cuff, the bottom and middle layers will separate by an amount sufficient to pneumatically connect the channeled passageway and the continuous pneumatic passageway.

4. The method of claim 2 including the step of regulating the pressure level of the pressurized gas.

5. The method of claim 2 including the step of sensing the pressure level of the pressurized gas.

6. The method of claim 1 wherein the sealing step includes extruding a bead of material adjacent to the sealed edge of the bladder between the bottom and middle layers; and the preventing step includes sizing the bead to separate the bottom and middle layers adjacent to the sealed edge by at least a selected amount that is greater than the separation between the middle and top layers adjacent to the sealed edge.

7. A method of making an elongated tourniquet cuff having a bladder that may be secured around the limb of a patient when deflated, comprising the steps of:
sealing together side edges of top, middle and bottom layers to form a gas-inflatable bladder between the bottom and middle layers;
preventing the two layers of the bladder from contacting each other at a location adjacent to a sealed edge of the bladder thereby to provide a continuous pneumatic passageway adjacent to the sealed edge for distributing inflating gas along the length of the bladder, including forming and sizing a bead to separate the bottom and middle layers adjacent to the sealed edge by at least a selected amount that is greater than the separation between the middle and top layers adjacent to the sealed edge, wherein the bead is disposed completely between the bottom and middle layer;

providing a port opening into the sealed bladder;

separating the bottom and middle layers adjacent to the port opening with a flange member that together with the bottom layer defines a channeled passageway extending away from the port opening for delivering pressurized gas from the port opening through the channeled passageway, beyond the flange member, and into the inflatable bladder.

8. The method of claim 7 wherein the step of separating the bottom and middle layers adjacent to the port opening with a flange member includes providing a flange member that includes one or more channels therein that extend between the two layers and away from the port opening for delivering gas through the one or more channels, between the two layers, and into the inflatable bladder.

9. The method of claim 7 wherein the step of sealing together the side edges of the top, middle and bottom layers to form the gas-inflatable bladder and the step of preventing the bottom and middle layers of the bladder from contacting each other at a location adjacent to a sealed edge of the bladder are performed substantially simultaneously.

10. The method of claim 7 including the step of extruding the bead, thereby forming and sizing a bead to separate the bottom and middle layers by at least a selected amount.

11. The method of claim 7 wherein the step of separating the bottom and middle layers adjacent to the port opening with a flange member includes sizing the flange member to have a diameter substantially greater than the diameter of the port opening into the sealed bladder.

12. The method of claim 7 including the step of including a tube having one end connected to a port member at the port opening into the sealed bladder and another end connected to a tourniquet instrument and having a passageway for providing inflation gas to the bladder and for monitoring the gas pressure therein.

13. The method of claim 12 including the step of connecting the tube to the instrument with a connector that has a passageway cross-sectional area that is not less than the cross-sectional area of the tube passageway.

14. The method of claim 12 including the step of shaping the tube to have an internal pneumatic passageway comprising a non-circular cross-sectional shape.

15. The method of claim 14 including the step of shaping the tube to have a ridge adjacent to the internal pneumatic passageway that extends from the instrument to the port opening.

16. The method of claim 12 including the step of adding to the tourniquet cuff an indicator that is reactive to an agent that is capable of affecting the integrity of the channeled passageway or the pneumatic passageway that is adjacent to the sealed edge, wherein the indicator produces an indication if the agent reaches a selected level.

17. The method of claim 16 wherein the adding step includes adding an indicator that is remotely detectable by the tourniquet instrument.

18. The method of claim 7 including the steps of:

positioning a stiffener member between the top layer and the middle layer to overlay the bladder and sizing the stiffener member to be narrower than the bladder to prevent the stiffener member from overlaying the continuous pneumatic passageway adjacent to the sealed edge.

19. The method of claim 18 wherein the step of positioning includes providing the stiffener member with a hole therethrough that aligns with the port opening.

20. The method of claim 18 further comprising the step of attaching fasteners to the cuff for enabling the bladder to be securely and snugly wrapped around the limb of a patient with the portion of the bladder underlying the stiffener member compressed between the stiffener member and the patient's limb.

21. A method of making an elongated tourniquet cuff having a bladder that may be secured around the limb of a patient when deflated, comprising the steps of:

sealing together side edges of top, middle and bottom layers to form a gas-inflatable bladder between the bottom and middle layers;

preventing the two layers of the bladder from contacting each other at a location adjacent to a sealed edge of the bladder thereby to provide a continuous pneumatic passageway adjacent to the sealed edge for distributing inflating gas along the length of the bladder, including forming and sizing the sealed-together edges of the bottom and middle layers to separate the bottom and middle layers adjacent to the sealed edge by at least a selected amount that is greater than the separation between the middle and top layers adjacent to the sealed edge;

providing a port opening into the sealed bladder;

separating the bottom and middle layers adjacent to the port opening with a flange member that together with the bottom layer defines a channeled passageway extending away from the port opening for delivering pressurized gas from the port opening through the channeled passageway, beyond the flange member, and into the inflatable bladder.

22. The method of claim 21, wherein the sealing step includes the substep of simultaneously sealing together side edges of top, middle and bottom layers to form a gas-inflatable bladder between the bottom and middle layers.

* * * * *